United States Patent [19]

Takemori et al.

[11] Patent Number: 4,999,185

[45] Date of Patent: Mar. 12, 1991

[54] COMPOSITION FOR ORAL CAVITY

[75] Inventors: Toshio Takemori, Tokyo; Tsutomu Arakawa, Urawa; Teruo Matsumoto, Kurume; Takashi Maruyama, Hino, all of Japan

[73] Assignee: Lotte Company Limited, Tokyo, Japan

[21] Appl. No.: 358,640

[22] Filed: May 30, 1989

[30] Foreign Application Priority Data

May 31, 1988 [JP] Japan ................. 63-131367

[51] Int. Cl.$^5$ .................. A61K 7/26; A61K 9/68; A61K 35/78
[52] U.S. Cl. ........................... 424/58; 424/48; 424/440; 424/441; 424/195.1; 426/631; 426/584; 426/660; 426/3
[58] Field of Search ............... 424/58, 195.1, 48, 440, 424/441; 426/631, 584, 3

[56] References Cited

U.S. PATENT DOCUMENTS 4,242,323 12/1980 Vlock ..................... 424/58

FOREIGN PATENT DOCUMENTS 1033186 6/1966 United Kingdom ............ 47/9

OTHER PUBLICATIONS

Kirk-Othmer Encyclopedia of Chemical Technology (3rd ed.), vol. 6, pp. 1–18 (1979), John Wiley & Sons, New York, N.Y., "Chocolate & Cocoa".
Hocking, A Dictionary of Terms in Pharmacognosy, Chas. Thomas, Springfield, Ill. (1955), p. 227 "*Theobroma cacao*".

Primary Examiner—Shep K. Rose
Attorney, Agent, or Firm—Young & Thompson

[57] ABSTRACT

A composition for inhibiting sordes formation is adapted for application to the oral cavity and contains an amount of isolated cacao husk extract effective to inhibit sordes formation. The cacao husk extract is extracted from cacao husks with a polar solvent. It has been found that the composition according to the invention inhibits glucosyltransferase activity, and thereby inhibits glucan synthesis. The composition may take the form of chocolates, stick gum, candy, biscuits, chocolate milk or ice cream incorporating the extract, or the extract may also be formulated as a tablet, toothpaste or mouthwash.

6 Claims, 1 Drawing Sheet

COMPOSITION FOR ORAL CAVITY

FIELD OF THE INVENTION

The present invention relates to a material having an effect of inhibiting sordes formation and a composition for oral cavity containing it which may be a sordes inhibiting agent or a sordes inhibiting food or drink, more specifically, relates to a component which is extracted from naturally occuring substance and may inhibit glucosyltransferase activity which catalyses glucan synthesis to cause sordes, and relates to a composition for oral cavity containing it.

BACKGROUND OF THE INVENTION

It is considered that sordes formation is an important cause of tooth decay. Namely, there is a convincing hypothesis in which tooth decay may proceed by converting sucrose in food to viscous polysaccharide glucan by glucosyltransferase which is an extracellular enzyme of *Streptococcus mutans,* so that the glucan adheres to the tooth to form sordes, resulting in decrease of pH of tooth surface by organic acids produced by microorganisms which proliferate in the sordes, resulting in destruction of the enamel portion. There are proposed as a method for preventing tooth decay a method for inhibiting sordes formation, a method for preventing acid production by microorganisms in sordes, or a method for decomposing and removing formed sordes.

Since the causing substance of sordes formation is glucan, it is necessary for reducing sordes formation to reduce glucan formation. For this purpose, several substances are conventionally proposed as substances for inhibiting sordes formation. For example, a sordes inhibiting agent comprising flavonoid is disclosed in Japanese laid-open patent application No. 59-13721, a sordes inhibiting agent composition containing chitin or chitosan is disclosed in Japanese laid-open patent application No. 61-151112, a composition for oral cavity containing γ-linolenic acid and/or linoleic acid having a tooth decay preventing effect is disclosed in Japanese laid-open patent application No. 61-260017, and a composition for oral cavity containing a seed oil of evening primrose is disclosed in Japanese laid-open patent application No. 61-268613.

It is ideally more desirable for a sordes formation inhibiting substance to be extracted from natural sources, especially from food materials which are anciently used as food to be acknowledged safe for human body, from a view of safety, than synthesized substances. Moreover, it is necessary for using that a composition used in the oral cavity have a good taste. Alternatively, even if a sordes formation inhibiting substance is extracted from natural substances those whose source is a natural substance that is different to obtain or requires a complex purification process has a problem of cost and is inconvenient to utilize industrially. Conventional materials for oral cavity which have an effect of inhibiting sordes formation do not fully satisfy all these requirements, among which obscure effects are provided, so that it is desired to develop a material for oral cavity which has more ideal effect for inhibiting sordes formation and to realize a composition for oral cavity containing it.

SUMMARY OF THE INVENTION

The object of the present invention is to provide a composition for oral cavity having an effective function for inhibiting sordes formation which has safety, good taste, is easy to obtain and extract, and which comprises an extract of a cheap material.

According to the present invention, there is provided a composition for oral cavity having an effect of inhibiting sordes formation characterized in that it contains an extract which is extracted from husk of cacao with a polar solvent.

PREFERRED EMBODIMENTS OF THE INVENTION

Figure 1:
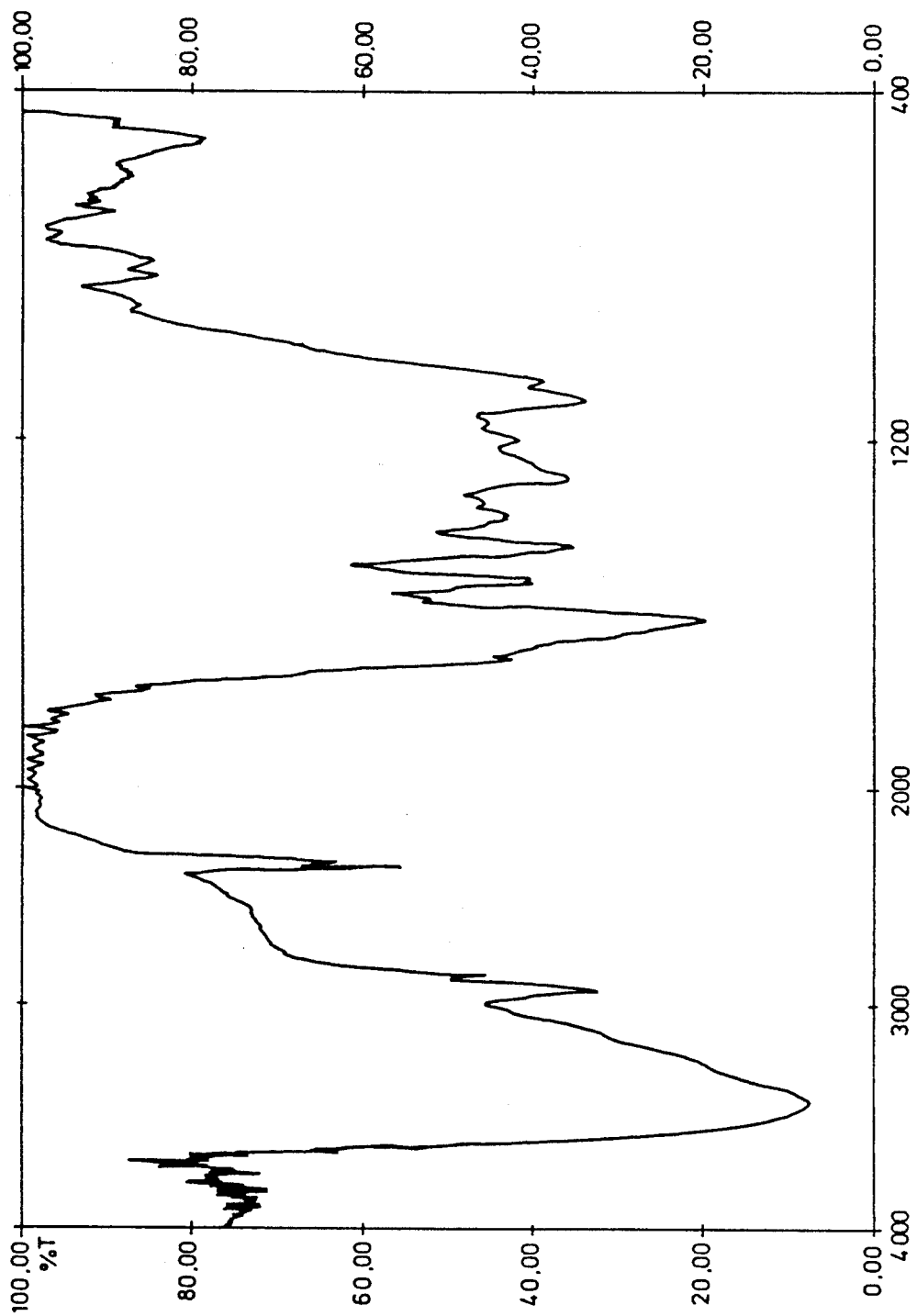
FIG. 1 is an IR chart of the water-insoluble fraction obtained in the Experiment 3 described herein. 10 scans were carried out with PERKIN-ELMER 1700 infrared spectrometer.

The husk of cacao is a hull of the seed (shell of the bean) of cacao (*Theobroma cacao* L.), for which those obtained during a production process of cocoa powder or chocolate or those obtained from an usual cacao bean (raw or fermented) may be used. The effect of the husk of cacao on the inhibition of sordes formation is first disclosed by the present invention.

In order to obtain the substance for inhibiting sordes formation, the husk of cacao is extracted with a polar solvent. The extraction temperature is not specifically limited, but a temperature between the room temperature and the reflux temperature of the solvent is preferable. The extraction time may be between 0.5-5 hours. The husk of cacao may be used intact, while it is preferable to use after grinding or forming to powder to make the extraction efficiency good. Alternatively, the husk may be extracted after treatment with nonpolar solvent to remove fat.

As a polar solvent, water, alkaline water, alcohol, water-containing alcohol, water-containing acetone or the like may be used. It is preferable as the polar solvent to use alkaline polar solvent, water-containing acetone or alkaline water-containing acetone.

A substance for inhibiting sordes formation is obtained by removing the solvent from the resulting extract solution as a solid. This may be used as a component of a composition for oral cavity to realize an effective sordes formation inhibiting effect.

It is postulated that the formation of sordes occurs by converting sucrose in food to the viscous polysaccharide glucan by glucosyltransferase which is an extracellular enzyme of *Streptcoccus mutans,* and adhering to accumulate the glucan on tooth. The extract of the present invention extracted from the husk of cacao with the polar solvent significantly inhibits the glucan synthesis by glucosyltransferase from *Streptcoccus mutans.* Therefore, the viscous adhering polysaccharide is not formed in the oral cavity, so that saccharides in food are rapidly removed to disappear directly from the oral cavity without suffering the function of *Streptcoccus mutans* in the sordes. The absence of formation of polysaccharides contributes reduction of the formation of sordes itself, and the absence of remaining monosaccharide in the oral cavity contributes reduction of the amount of microorganisms which grow with it as a substrate and also contributes reduction of organic acid to be formed.

The husk of caca is the hull of cacao which is a food material, which has been anciently used as food by human beings and is recognized as harmless to the human body, so that there is no problem in safety, as well as it has a good taste. The husk of cacao may be considered to be a kind of waste of byproduct from the production process of cocoa powder or chocolate. There has been conventionally few usage thereof except for a raw material for feed for livestock or natural pigment. According to the present invention, the husk of cacao as an waste may be effectively utilized, so that an extract may be prepared by relatively conveniently extracting from an easily obtainable and cheap material to obtain a composition for oral cavity containing it having an effective inhibiting function for sordes formation.

According to the present invention, there is provided a composition for oral cavity having an effective function for inhibiting sordes formation which has safety, good taste, is easy to obtain and easy to extract, and which comprises an extract of a cheap material.

Experiments 104 and Examples 1-9

The present invention will be explained in detail with following examples, to which the present invention is not to be constructed as limited. At first, preparations of extracts of husk of cacao extracted with several polar solvents will be shown as Experiments, and then a test of inhibiting glucosyltransferase activity from *Streptococcus mutans* with the above extracts will be shown, after which concrete formulations of the composition for oral cavity of the present invention will be shown as Examples.

PREPARATION OF EXTRACTS OF HUSK OF CACAO

Experiment 1

500 ml of petroleum ether is added to 50 g of a husk of cacao, which is agitated for 1 hour, and then petroleum ether is removed by filtration to obtain a nonfat husk. 70% acetone-water is added to it to extract at 60° C. for 1 hour. After removing solid by centrifugation of the extract solution, acetone is removed by evaporation to lyophilize to obtain 5.7 g of brown powder.

Experiment 2

2000 g of powder of husk of cacao is effected to fat-removing with 3000 ml of hexane, and the residue is dried, which is extracted with 2000 ml of 0.05 N NaOH aqueous solution for 2 hours. A filtrate obtained by filtration of the extract solution is adjusted to pH 7.5, after which 394 g of brown powder is obtained by lyophilization.

Experiment 3

1000 ml of ethanol is added to 100 g of powder which is obtained as the Experiment 1, and extraction is carried out at room temperature for 1 hour. After filtration, a residue is obtained as an ethanol-insoluble fraction. 1000 ml of water is added to the ethanol-insoluble fraction, and extraction is carried out at room temperature for 1 hour. After filtration, 4 g of dark-brown residue is obtained as an water-insoluble fraction. And the filtrate is lyophilized to obtain 71 g of brown powder as an water-soluble fraction. IR spectrum of the water-insoluble fraction is shown in FIG. 1.

Experiment 4

500 ml of petroleum ether is added to 50 g of husk of cacao, and agitation is carried out for 1 hour, petroleum ether layer is removed by filtration to obtain a nonfat husk. A mixture of acetone/0.01 N NaOH aqueous solution (1:1) is added, and extraction is carried out at 40° C. for 2 hours. After the solid is removed from the extract solution by centrifugation, neutralization is carried out, acetone is removed, and 5.9 g of brown powder is obtained by lyophilization.

Test of inhibition of glucosyltransferase activity

Polar solvent extracted fractions obtained from Experiments 1-4 and the white solid obtained by extraction from husk with petroleum ether are dissolved or dispersed at a constant concentration to use as test solutions, in order to carry out a test of inhibition of glucosyltransferase activity as follows.

Glucosyltransferase from *Streptococcus mutans* B13 is prepared with an usual method. By using it, a test of synthesis inhibition of glucan which adheres to the wall of test tube is carried out as follows.

0.05 M potassium phosphate buffer containing 37.5 mg of sucrose (pH 6.5, 0.02% NaN3) 800 $\mu$, glucosyltransferase solution 20 $\mu$l, water 80 $\mu$l, test solution 100 $\mu$l are added to a test tube to fully mix, and this tube is incubated for 16 hours at 37° C. declining to an angle of 30° from the horizontal plane. The reaction solution is removed by decantation, and 6 ml of water is added to the tube to disperse the adhered glucan on the wall of the test tube by ultrasonic treatment. Absorbance at 550 nm is measured to calculate an inhibition ratio of synthesis of adhered glucan with the following formula. ps Inhibition ratio(%) = (1 − absorbance of tested/absorbance of control) × 100 Obtained results are shown in Table 1.

TABLE 1

| Tested solution | | Absorbance | Inhibition ratio (%) |
|---|---|---|---|
| Extract from Experiment 1 | 100 μg/ml | 0.011 | 96.1 |
| | 10 μg/ml | 0.276 | 2.5 |
| Extract from Experiment 2 | 100 | 0.002 | 99.3 |
| | 10 | 0.155 | 45.2 |
| Soluble fraction from Experiment 3 | 100 | 0.002 | 99.3 |
| | 10 | 0.207 | 26.9 |
| Insoluble fraction from Experiment 3 | 100 | 0.003 | 98.9 |
| | 10 | 0.017 | 94.0 |
| Extract from Experiment 4 | 100 | 0.001 | 99.6 |
| | 10 | 0.142 | 49.8 |
| Extract with petroleum ether | 100 | 0.265 | 6.4 |
| | 10 | 0.279 | 1.4 |
| Control (water) | | 0.283 | 0 |

From Table 1, it is shown that in tests in which effective amount of extracts of Experiments 1-4 are added, the enzyme activity of glucosyltransferase is greatly decreased by the inhibitory function of extracts, and sucrose is not converted to glucan which adheres on the surface of test tube, so that the absorbance (turbidity) which was measured after ultrasonic treatment for scattering and dispersing all glucan adhered on the wall of test tube into water after addition of water after reaction is reduced.

FORMULATIONS OF COMPOSITIONS FOR ORAL CAVITY

Example 1

| Chocolate | |
|---|---|
| Cacao bitter | 20 parts |
| Cacao butter | 17 |
| Sugar | 43 |
| Raw-fat power milk | 20 |
| Extract from Experiment 1 | 0.4 |
| Flavor | 0.2 |

Example 2

| Stick gum | |
|---|---|
| Gum base | 20 parts |
| Sugar | 55 |
| Glucose | 15 |
| Corn syrup | 9.1 |
| Flavor | 0.8 |
| Extract from Experiment 4 | 0.1 |

Example 3

| Candy | |
|---|---|
| Granulated sugar | 50 parts |
| Corn syrup (D.E. 42) | 50 |
| Water | 20 |
| Extract from Experiment 2 | 0.2 |

Example 4

| Tablet confection | |
|---|---|
| Sugar | 80 parts |
| Lactose | 20 |
| Sucrose fatty acid ester | 0.16 |
| Water | 4.5 |
| Extract from Experiment 1 | 0.1 |

Example 5

| Biscuit | |
|---|---|
| Soft wheat flour | 100 parts |
| Shortening | 30 |
| Powder sugar | 32 |
| Corn syrup (D.E. 42) | 5 |
| Nonfat powder milk | 1.8 |
| Table salt | 1.1 |
| Leavening agent | 0.45 |
| Water-insoluble fraction from Experiment 3 | 0.1 |

Example 6

| Drink (Milk cocoa) | |
|---|---|
| Sugar | 80 parts |
| Raw-fat condensed milk | 55 |
| Nonfat powder milk | 15 |
| Cocoa powder | 10 |
| Emulsifier | 0.5 |
| Stabilizer | 0.5 |
| Flavor | 0.5 |

| Drink (Milk cocoa) -continued | |
|---|---|
| Water-soluble fraction from Experiment 3 | 0.2 |
| Water | 1000 |

Example 7

| Ice cream | |
|---|---|
| Coconut oil | 10.5 parts |
| Sugar | 12 |
| High fructose corn syrup | 4 |
| Corn syrup (D.E. 42) | 6 |
| Emulsifier | 0.2 |
| Stabilizer | 0.2 |
| Flavor | 0.3 |
| Extract from Experiment 1 | 0.1 |

Example 8

| Toothpaste | |
|---|---|
| Calcium secondary phosphate dihydrate | 45 parts |
| Carboxymethyl cellulose | 1 |
| Glycerol | 20 |
| Sodium lauryl sulfate | 1.5 |
| Flavor | 1 |
| Saccharin | 0.1 |
| Extract from Experiment 2 | 0.2 |
| Water | 30 |

Example 9

| Mouth washing agent | |
|---|---|
| Ethanol | 70 parts |
| Glycerol | 30 |
| Polyoxyethylene hardened castor oil | 2.0 |
| Saccharin | 0.2 |
| Flavor | 2.0 |
| Extract from Experiment 4 | 0.1 |
| Water | 90 |

The compositions for oral cavity according to the present invention formulated hereinbefore have an effective function of inhibiting sordes formation, and are of course harmless to human body having a good taste.

What is claimed is:

1. A chocolate composition for application to the oral cavity, containing an amount of an isolated cacao husk extract effective to inhibit sordes formation, said extract having been extracted from cacao husks with a polar solvent.

2. The chocolate composition according to claim 1, wherein the extract is in powder form and is substantially free of synthesized substances.

3. The chocolate composition according to claim 1, wherein the polar solvent is an alkaline polar solvent.

4. The chocolate composition according to claim 1, wherein the polar solvent is water-containing acetone.

5. The chocolate composition according to claim 1, wherein the polar solvent is alkaline water-containing acetone.

6. The chocolate composition according to claim 1, wherein said amount of said extract ranges, on a dry weight basis, from about 0.01 to about 0.4% by weight of said composition.

* * * * *